United States Patent
Sherman et al.

(10) Patent No.: US 9,486,190 B2
(45) Date of Patent: Nov. 8, 2016

(54) SPRAY DELIVERY SYSTEM

(75) Inventors: Ethan G. Sherman, Jacksonville, FL (US); David J. Little, Ponte Vedra, FL (US); Wei Chen, St. Johns, FL (US); John R. Prisco, Jacksonville, FL (US); Matthew J. Friend, St. Augustine, FL (US); Matthew F. Myntti, St. Augustine, FL (US); Tom Zelmer, Raleigh, NC (US); Cyan Godfrey, Chapel Hill, NC (US); Roy Attride, Raleigh, NC (US)

(73) Assignee: Medtronic Xomed, Inc., Jacksonville, FL (US)

( * ) Notice: Subject to any disclaimer, the term of this patent is extended or adjusted under 35 U.S.C. 154(b) by 635 days.

(21) Appl. No.: 13/284,600

(22) Filed: Oct. 28, 2011

(65) Prior Publication Data

US 2013/0110161 A1    May 2, 2013

(51) Int. Cl.
*A61B 17/00* (2006.01)

(52) U.S. Cl.
CPC .......... *A61B 17/00491* (2013.01); *A61B 2017/00495* (2013.01); *A61B 2017/00522* (2013.01)

(58) Field of Classification Search
CPC .......... A61B 17/00491; A61B 2017/00522; A61B 2017/00495; B05B 7/0416; B05B 7/0483; B05B 7/0408; B05B 7/025; B01F 13/0023; A61C 5/064; A61M 2005/3139; A61M 2005/3131; A61M 2005/3132; A61M 2005/3142; A61M 2005/1787; A61M 5/3137; A61M 5/31501; A61M 5/19
USPC .......... 606/214, 213; 604/82, 19, 191, 187, 604/181, 93.01, 290, 506, 173, 257, 235, 604/242, 243, 258, 259, 240; 222/129, 222/145.1, 145.5, 145.6, 135
See application file for complete search history.

(56) References Cited

U.S. PATENT DOCUMENTS

| | | | |
|---|---|---|---|
| 1,906,991 A | 5/1933 | McTernan | |
| 4,700,894 A | 10/1987 | Grzych | |
| 4,735,616 A * | 4/1988 | Eibl et al. | 604/191 |
| 4,950,231 A | 8/1990 | Liu | |
| 5,290,259 A * | 3/1994 | Fischer | 604/218 |
| 5,464,396 A | 11/1995 | Barta et al. | |
| 5,582,596 A * | 12/1996 | Fukunaga et al. | 604/191 |
| 5,788,667 A | 8/1998 | Stoller | |
| 6,112,743 A | 9/2000 | Denton | |
| 6,234,994 B1 * | 5/2001 | Zinger | 604/82 |
| 6,319,248 B1 | 11/2001 | Nahon | |
| 6,471,670 B1 * | 10/2002 | Enrenfels et al. | 604/88 |
| 6,589,216 B1 | 7/2003 | Abbott et al. | |
| 6,926,711 B2 | 8/2005 | Lentz et al. | |
| 6,936,033 B2 | 8/2005 | McIntosh et al. | |

(Continued)

FOREIGN PATENT DOCUMENTS

| | | |
|---|---|---|
| DE | 3108918 A1 | 9/1982 |
| EP | 0363519 A1 | 4/1990 |

(Continued)

OTHER PUBLICATIONS

Wolfe Tory Medical, Inc. Brochure, "It's MADgic Laryngo-Tracheal Mucosal Atomization Device".

*Primary Examiner* — Jocelin Tanner
(74) *Attorney, Agent, or Firm* — IPLM Group, P.A.

(57) ABSTRACT

A delivery system for delivering multiple components that is assembled using snap-fit assembly and threadless engagement of syringes and associated parts.

17 Claims, 8 Drawing Sheets

(56) References Cited

U.S. PATENT DOCUMENTS

| | | |
|---|---|---|
| 6,976,979 B2 | 12/2005 | Lawrence et al. |
| 7,322,956 B2 * | 1/2008 | Fehr et al. ............... 604/82 |
| 7,455,248 B2 | 11/2008 | Kablik et al. |
| 7,635,343 B2 | 12/2009 | McIntosh et al. |
| 7,637,901 B2 | 12/2009 | Lawrence et al. |
| 8,530,632 B2 | 9/2013 | Tijsma et al. |
| 2002/0032463 A1 * | 3/2002 | Cruise et al. ............ 606/214 |
| 2002/0055723 A1 | 5/2002 | Liu et al. |
| 2002/0177840 A1 | 11/2002 | Farnholtz |
| 2004/0059283 A1 | 3/2004 | Kirwan et al. |
| 2004/0087932 A1 | 5/2004 | Lawrence et al. |
| 2005/0096588 A1 | 5/2005 | Hagmann et al. |
| 2005/0119609 A1 | 6/2005 | McLean |
| 2006/0020256 A1 | 1/2006 | Bell et al. |
| 2006/0219735 A1 | 10/2006 | Faye et al. |
| 2006/0253082 A1 | 11/2006 | McIntosh et al. |
| 2007/0005020 A1 | 1/2007 | Laveault |
| 2008/0183128 A1 | 7/2008 | Morriss et al. |
| 2008/0249483 A1 | 10/2008 | Slenker et al. |
| 2009/0076459 A1 * | 3/2009 | Goldberg ................. 604/191 |
| 2009/0209916 A1 | 8/2009 | Peindl et al. |
| 2009/0270346 A1 | 10/2009 | Tijsma et al. |
| 2009/0285897 A1 * | 11/2009 | Myntti et al. ............ 424/488 |
| 2009/0291912 A1 | 11/2009 | Tijsma et al. |
| 2010/0072303 A1 | 3/2010 | Hayakawa |
| 2010/0298642 A1 | 11/2010 | Trusty et al. |
| 2011/0092892 A1 | 4/2011 | Nitsan et al. |
| 2013/0066297 A1 | 3/2013 | Shtul et al. |

FOREIGN PATENT DOCUMENTS

| | | |
|---|---|---|
| EP | 2145599 A1 | 1/2010 |
| JP | HEI 8-19619 | 1/1996 |
| JP | 2003-38646 | 2/2003 |
| JP | 2006-326064 | 12/2006 |
| WO | 9619940 A1 | 7/1996 |
| WO | 9932185 A1 | 7/1999 |
| WO | 0071016 A1 | 11/2000 |
| WO | 0167961 A1 | 9/2001 |
| WO | 2004041424 A1 | 5/2004 |
| WO | 2005094665 A2 | 10/2005 |
| WO | 2008057802 A2 | 5/2008 |
| WO | 2009124407 A1 | 10/2009 |
| WO | WO 2009/132226 A1 | 10/2009 |
| WO | WO 2009/132228 A1 | 10/2009 |
| WO | 2010009563 A1 | 1/2010 |
| WO | 2010091527 A1 | 8/2010 |

* cited by examiner

SPRAY DELIVERY SYSTEM

TECHNICAL FIELD

This invention relates to multi-component spray delivery systems.

BACKGROUND

Sinusitis is an inflammation of the mucosal tissue lining of the sinus walls which may lead to nasal passageway blockage, mucous stagnation and bacterial or fungal sinus cavity infection. Typical treatments begin with antibiotics. However, when antibiotics cannot relieve sinusitis, sinus surgery (which involves opening the sinus cavities and removing mucosal tissue) may be an alternative. Post-operative care for such surgery requires temporary and uncomfortable sinus packing or gauze which supports the reopened sinus passage and absorbs excess fluid while the tissues heal. After several days or at the discretion of the physician, the gauze packing is removed. Doing so is painful.

Sinus sealants and other biological materials have emerged as a promising technique to temporarily seal or otherwise protect the post-operative passageways with less intrusion and pain than that caused by traditional packing techniques.

SUMMARY OF THE INVENTION

Biomaterials have been used in ear, nose, and throat (ENT) procedures for surgical repair and drug delivery. The chemical nature of some biomaterials requires that they be provided in a multi-component form with the components being separated prior to use. The components are mixed together shortly before or during delivery, and the mixture rapidly forms a gel or solid.

There are, however, potential difficulties when using highly-reactive multi-component biomaterial systems. If the components react too rapidly, the resulting mixture may exhibit poor or erratic performance. Rapid reaction may however be desired for other reasons, such as a need for the biomaterial system to be spray-applied yet quickly form a gel or solid at a desired application site. An operator also desirably should be able to dispense the biomaterial using a single gloved hand.

The invention provides, in one aspect, a spray delivery system comprising:
  a) a body having a syringe-receiving portion and a finger grip portion, the body configured to receive and capture at least two liquid-containing syringes;
  b) an actuating member that operates on the at least two syringes to provide simultaneous syringe content delivery;
  c) a manifold configured to receive liquid contents of the at least two syringes; and
  d) a spray head that receives liquids from the manifold; and
wherein the at least two syringes are captured by the body and connected to the manifold without requiring threaded engagement.

BRIEF DESCRIPTION OF THE DRAWING

Like reference symbols in the various figures of the drawing indicate like elements. The elements in the drawings are not to scale.

DETAILED DESCRIPTION

The recitation of a numerical range using endpoints includes all numbers subsumed within that range (e.g., 1 to 5 includes 1, 1.5, 2, 2.75, 3, 3.80, 4, 5, etc.).

Figure 1:
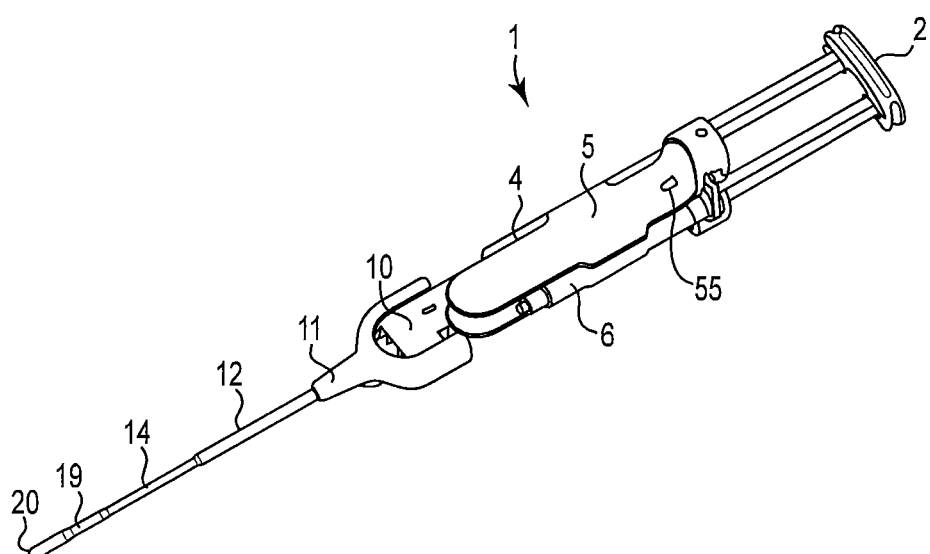
FIG. 1 is a schematic view of an exemplary spray delivery system.

FIG. 1 shows an exemplary medical spray delivery system or apparatus 1 that can deliver a mixture of fluid components at substantially at the same time, yet maintain the components separate from one another until just before delivery to a target site. The components may be multiple agents such as multiple component tissue sealants (e.g. two components) delivered to a variety of bodily passageways or cavities including nasal cavities and sinus cavities (e.g. maxillary, frontal or sphenoid sinuses). Exemplary multi-component tissue sealants may include reactive polysaccharides, for example, chitosan and starch. Other exemplary multi-component tissue sealants are provided in U.S. patent application Ser. No. 12/429,141, now published as U.S. Patent Application Publication No. US2009/0270346A1 and U.S. patent application Ser. No. 12/429,150, now published as U.S. Patent Application Publication No. US2009/0291912A1.

FIG. 1, which shows an exemplary spray delivery system 1, includes an actuating member 2 and body 5. Body 5 is capable of receiving and capturing syringes 4, 6. The spray delivery system 1 further includes cannula 14, the distal end of which terminates at spray head 20. Cannula 14 and spray head 20 are connected to body 5 through manifold 10. Manifold 10 may be surrounded by a shroud 11. Body 5 and manifold 10 are configured to receive portions of syringes 4, 6 and provide a liquid tight connection of the syringes 4, 6 to manifold 10 without requiring threaded engagement of syringes 4, 6 and manifold 10 (e.g., without a bayonet connection, mating screw threads or other thread-bearing connection requiring specific orientation and rotation steps to connect syringes 4, 6 and manifold 10). Support member 12 surrounds the outer portions of the proximal end of cannula 14, and provides additional rigidity to cannula 14. Towards the distal end of cannula 14 and adjacent spray head 20 a sheath 19 smoothes the interface between spray head 20 and cannula 14 and thereby facilitates insertion of cannula 14 into confined spaces.

The spray delivery system 1 may be used with a spray head 20 and a cannula 14 as shown in FIG. 1 and as described in detail in U.S. patent application Ser. No. and in U.S. patent application Ser. No. respectively, filed even date herewith and each of which is incorporated herein by reference in its entirety.

Figure 2A:
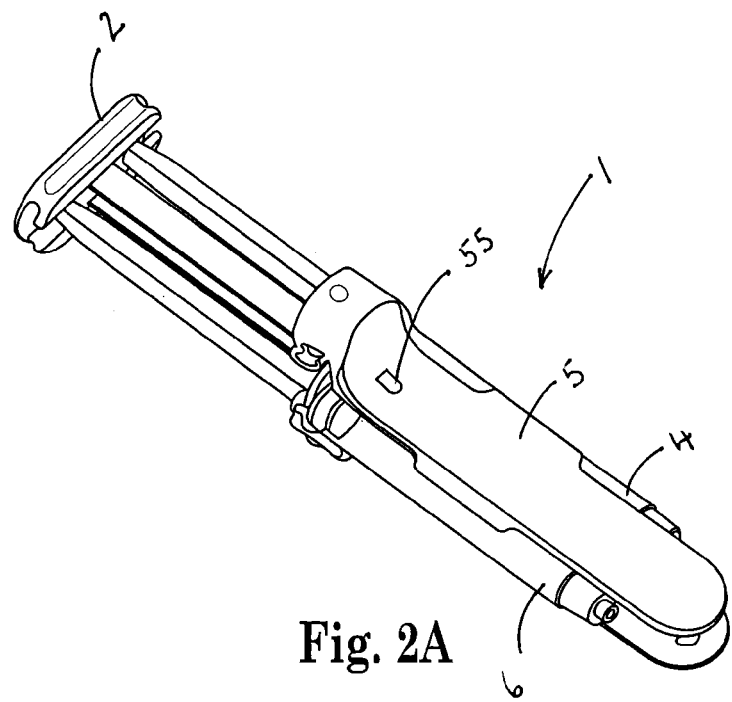
FIG. 2A is a perspective view of the FIG. 1 spray delivery system.
Figure 2B:
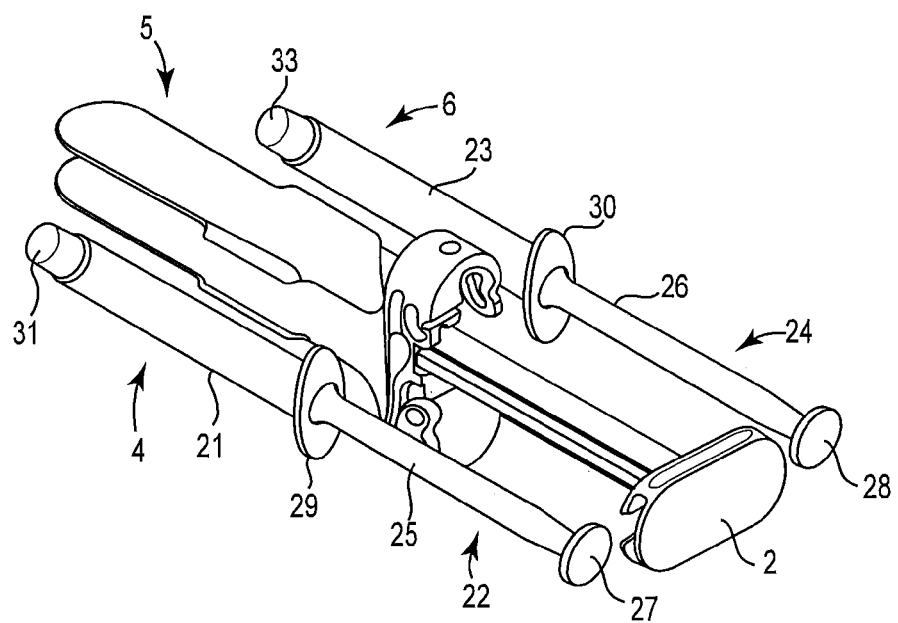
FIG. 2B is a exploded, perspective view of the FIG. 2A spray delivery system.

Referring to FIG. 2A and FIG. 2B, syringes 4, 6 have a syringe barrel 21, 23 where liquid contents are housed. The syringes 4, 6 can be the same size or can have different sizes, diameters or lengths. Associated with each syringe barrel 21, 23 is a syringe plunger 22, 24 which is inserted into the end of the syringe barrel 21, 23 in standard fashion so that as the syringe plunger 22, 24 is pushed into the syringe barrel 21, 23, the fluid contents of the barrel are dispensed. Each of the plungers 22, 24 has an elongated shaft 25, 26 and a push flange 27, 28 at the proximal end of the shaft 25, 26. At the proximal end of each syringe barrel 21, 23 are finger support flanges 29, 30. At the distal ends of syringe barrel 21, 23 are syringe outlets 31, 33.

Exemplary syringes may be or may be adapted from, for example, standard, commercially available syringes. Commercial syringes may include syringes from Becton Dickinson such as the LUER™-Slip syringes and LUER™-Lok syringes.

The syringe outlets 31, 33 preferably include a LUER™ taper (e.g., as described in ISO 594) or other standardized size or shape, and may be unthreaded or may include threaded (but unneeded) connecting portions such as those present in a LUER™-Lok syringe. Syringes 4, 6 engage body 5 and manifold 10 without requiring threaded engagement. Body 5 and syringes 4, 6 preferably are connected to manifold 10 by a latch 56, as shown in FIG. 3 and described in detail below.

Figure 3:
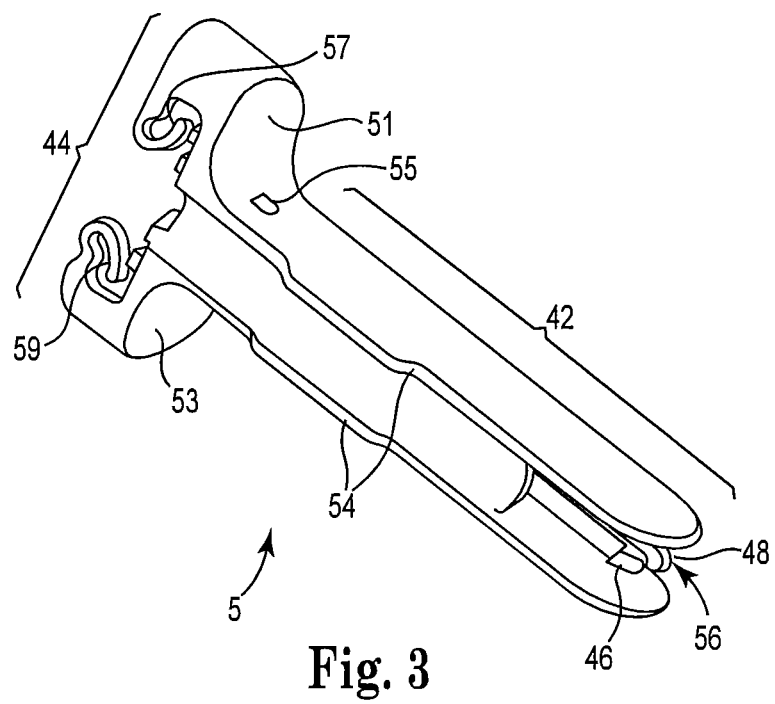
FIG. 3 is a perspective, side view of body 5 from FIG. 2B.

FIG. 3 shows an exemplary body 5 that may, for example, be made of molded plastic. Body 5 includes a syringe-receiving portion 42 and a finger-grip portion 44. Syringe-receiving portion 42 preferably is generally perpendicular to finger-grip portion 44. The syringe-receiving portion 42 is configured to securely receive and capture syringes 4, 6. Such a configuration may include, for example, outwardly-deflectable resilient sidewalls 54 (as shown in FIG. 3), which cooperate to provide a resilient cavity in body 5. The illustrated configuration facilitates capture of syringes 4, 6 in body 5 without requiring threaded engagement of syringes 4, 6. Although both hands may be used to assemble syringes 4, 6 into the spray delivery device 1, the illustrated configuration preferably permits single-handed placement of syringes 4, 6 by snapping syringes 4, 6 into resilient sidewalls 54. The force required to assemble a syringe into the resilient sidewalls 54 of body 5 may be, for example, less than about 20 lbf, preferably between 12-15 lbf.

Body 5 preferably is further configured to easily receive and engage the manifold 10, for example, through a snap-fit engagement. Such a snap-fit arrangement provides for a leak-free attachment that does not require adhesives or other fastening mechanisms, lowering manufacturing costs and providing for quick and easy assembly. The snap-fit engagement may include, for example, a latch 56, as illustrated in FIG. 3. Latch 56 preferably includes at least two projections 46, 48 that may be integral with body 5. The projections 46, 48 may, for example, end with angled overhangs, hooks, beads or slots to allow the body 5 to interlock with a mating surface or surfaces on manifold 10. The projections 46, 48 may, for example, briefly deflect inwardly when body 5 and manifold 10 are assembled. This arrangement may be designed for repeated assembly and disassembly, or for easy assembly and difficult disassembly.

The body 5 can also be connected to the manifold 10 with the use of a permanent or semi-permanent adhesive. The force required to assemble manifold 10 to body 5 may be, for example, about less than 20 lbf, preferably between 5-10 lbf, and the force required to disassemble manifold 10 from body 5 preferably is about greater than 20 lbf, more preferably between 25-30 lbf.

The finger-grip portion 44 may include a pair of positive pressure spring fingers 57, 59, as shown in FIG. 3, that aid in engaging a syringe portion, for example, finger support flanges 29, 30 and for securely holding and positioning the syringes 4, 6 in a substantially parallel manner and maintaining pressure biasing syringe outlets 31, 33 towards mating surfaces on the device, e.g. on body 5 or manifold 10, thereby assisting in maintaining a liquid-tight seal at syringe outlets 31, 33.

Figure 4:
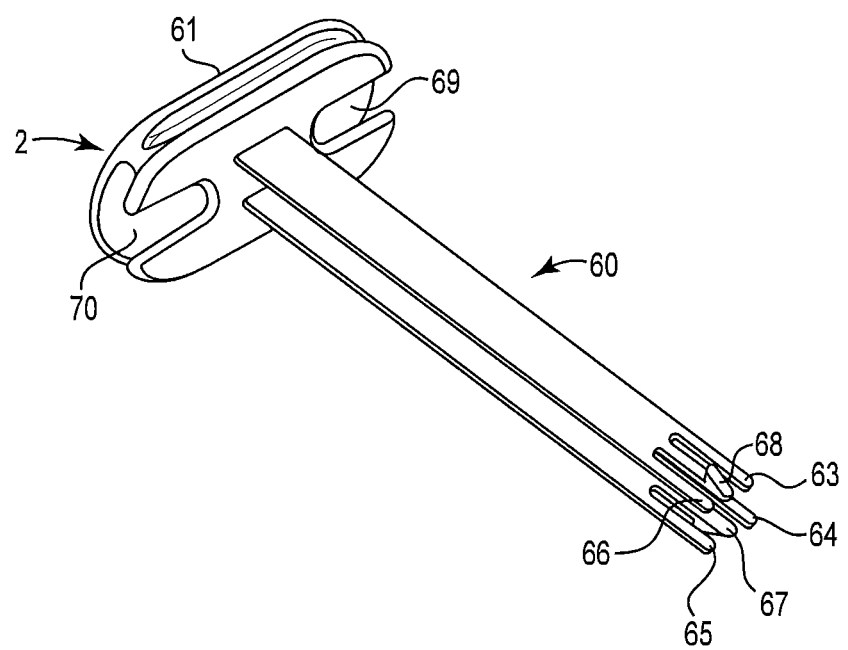
FIG. 4 is a perspective view of an actuating member.

Body 5 may be further configured to slidably receive within it actuating member 2. FIG. 4 illustrates an exemplary actuating member 2, which as shown, includes a guide rod 60 and a thumb press 61 oriented generally perpendicular to guide rod 60. The guide rod 60 may, for example, mate with complementary grooves within body 5. Guide rod 60 preferably terminates with projections such as the four needle-like projections 63, 64, 65, 66 and two angled resilient latch arms 67, 68 shown in FIG. 4. Latch arms 67, 68 preferably engage notch 55 (as shown in FIG. 2A) on body 5 so as to prevent unintentional removal of actuating member 2 during assembly or use of delivery system 1. For example, latch arms 67, 68 can be configured to engage notch 55 when thumb press 61 is first depressed. Actuation member 2 can also be preassembled with body 5. The force required to assemble actuating member 2 to body 5 may be, for example, less than about 5 lbf, preferably between 1-3 lbf.

Thumb press 61 preferably is configured to receive push flanges 27, 28 so that the two syringe plungers 22, 24 can be actuated substantially uniformly and simultaneously. Thumb press 61 desirably accommodates a variety of available push flange sizes and maintains them in substantial alignment with one another. As illustrated in FIG. 4, the thumb press 61 includes a pair of slots 69, 70 sized and shaped to receive push flanges 27, 28, and includes a contoured thumb depression for ergonomic delivery.

The force required to deliver biomaterials or gels using spray delivery device 1 may be, for example, about less than 10 lbf, preferably between 3-5 lbf.

Figure 5:
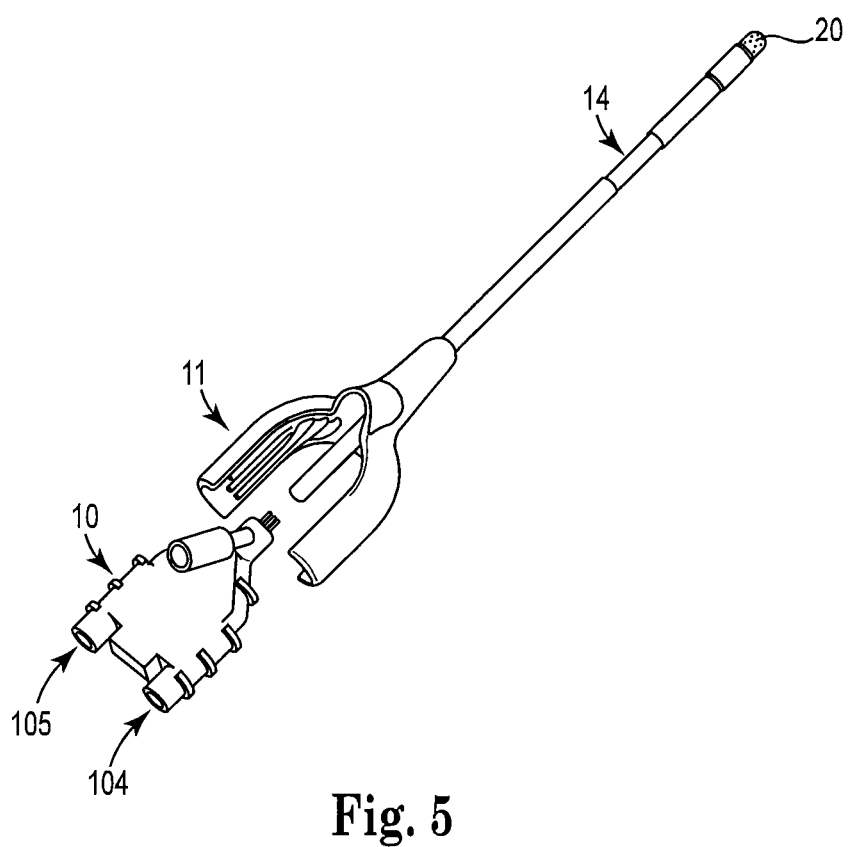
FIG. 5 is a perspective, exploded view of an exemplary manifold shown with a shroud, cannula and spray head.

FIG. 5 shows a partially assembled cannula 14 and spray head 20 with manifold 10. Manifold 10 attaches the body 5 to a cannula 14, and preferably delivers the liquid contents of syringes 4, 6 to spray head 20 while maintaining the liquids separate from one another until just before they exit spray head 20.

As illustrated in FIG. 5, a shroud or casing 11 may engage outer portions of manifold 10 and portions of cannula 14. The shroud 11 imparts additional rigidity to cannula 14 thereby aiding in maneuvering and navigating the distal end of the delivery device 1 within sinus or other bodily cavities. Shroud 11 may be removable but preferably is permanently attached to the manifold 10, for example, by adhesives, welding, snap or latch engagement, or injection molding.

Figure 6A:
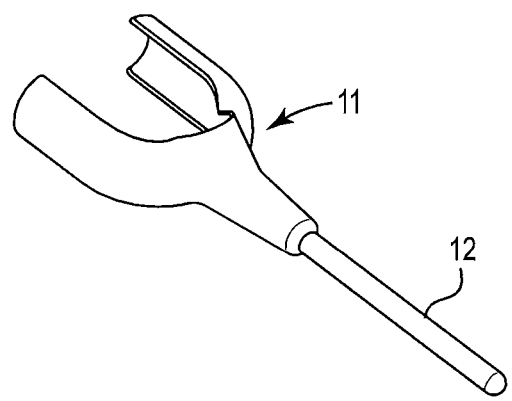
FIG. 6A is a perspective view of the FIG. 5 shroud.
Figure 6B:
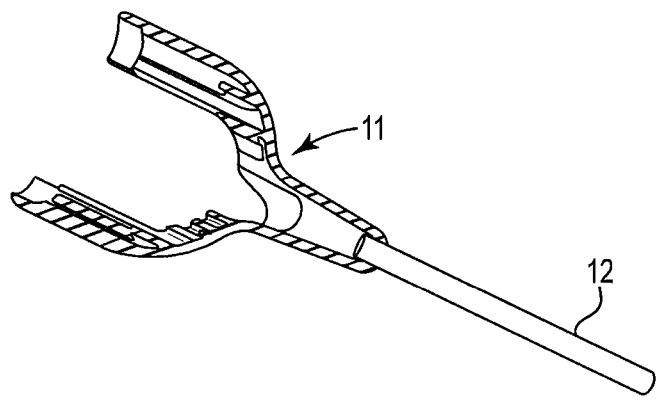
FIG. 6B is a perspective view, partially in cross-section of the FIG. 5 and FIG. 6A shroud.

FIG. 6A shows shroud 11 connected to support member 12 and FIG. 6B shows a partial cross sectional view of FIG. 6A that illustrates a preferred interface between shroud 11 and support member 12. Support member 12 shifts strain from cannula 14 to shroud 11 and away from the tip of manifold 10. The support member 12 may be, for example, made from a medically acceptable metal such as stainless steel or a medically acceptable polymer such as acrylonitrile butadiene styrene (ABS) or the like.

Figure 7:
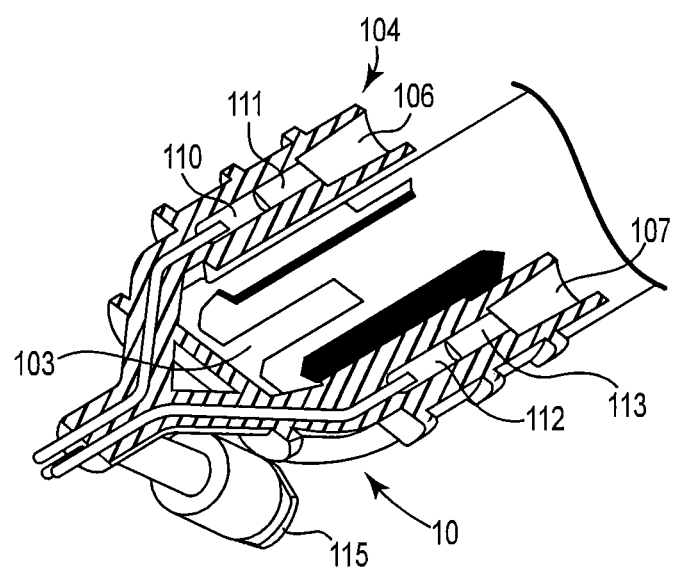
FIG. 7 is a cross-sectional view of a portion of the FIG. 5 manifold.

The manifold 10 may be further configured and arranged to interlock with body 5 by mating with latch 56. As shown in FIG. 7 and described above, the projections 46, 48 deflect inwardly when they pass through channel 103 in a central portion of manifold 10. As the projections 46, 48 pass the edge of the channel 103, the projections 46, 48 return to their original shape locking in place manifold 10 to the body 5.

Figure 8:
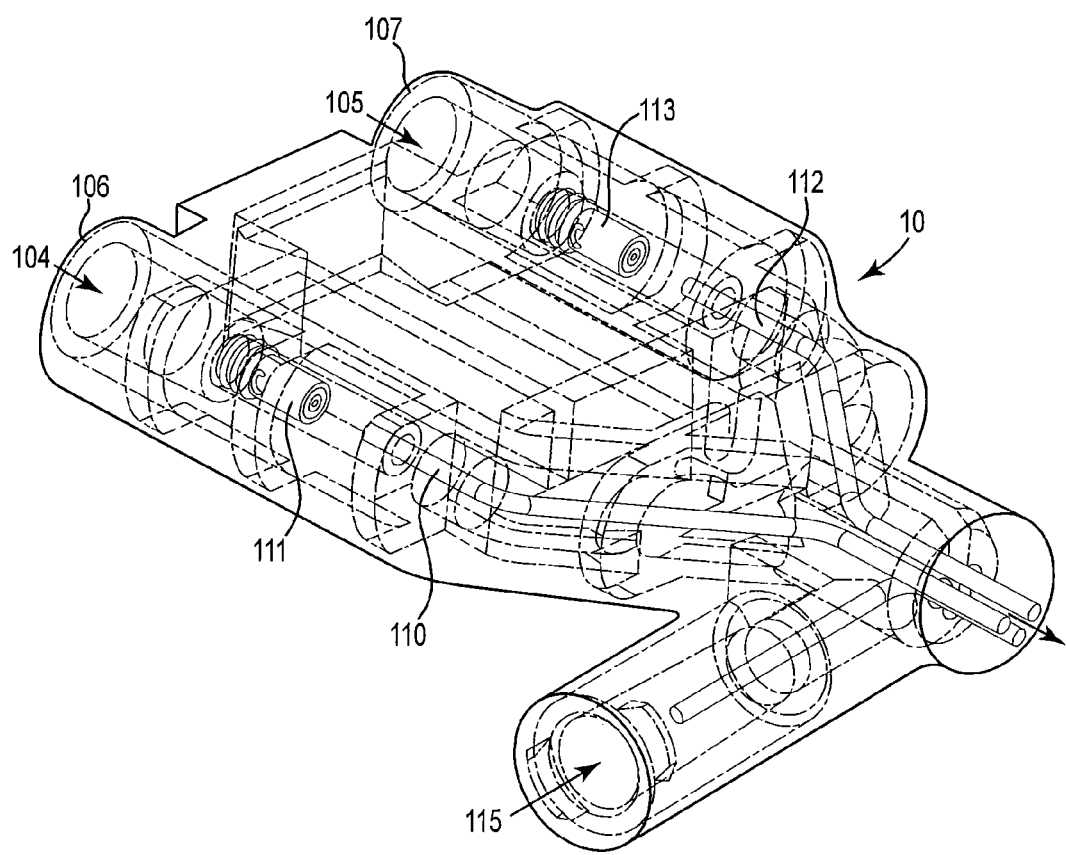
FIG. 8 shows the fluid flow path through the FIG. 5 manifold.

FIG. 8 shows preferred flow paths inside manifold 10. The internal portion of manifold 10 includes a first port 104 and second port 105 at the proximal end of manifold 10. First port 104 includes inlet opening 106 and second port 105 includes inlet opening 107. Openings 106, 107 are sized and shaped to receive syringe outlets 31, 33 without requiring threaded engagement of syringes 4, 6 into manifold 10.

The manifold 10 further includes a first fluid channel 110 and a second fluid channel 112. First fluid channel 110 may be operatively connected to and in fluid communication with syringe 4. Second fluid channel 112 is operatively connected to and in fluid communication with syringe 6. As shown in FIG. 8, liquids delivered from syringes 4, 6 to first fluid channel 110 and second fluid channel 112 pass through one-way check valves 111, 113, respectively. Check valves 111, 113 permit flow from the syringes 4, 6 through channels 110, 112 while preventing backflow of gas or the syringe contents.

Syringe outlets 31, 33 may be engaged to first port 106 and second port 107 respectively, for example, by a taper fitting, push fitting, press-on fitting or other frictional fitting that does not require threaded engagement. Preferably, engagement is via the tapered end portion of a LUER™ connection.

Manifold 10 may also include a gas inlet 115, as shown in FIG. 8, for supplying compressed gas to the multi-component mixture. Doing so can help expel the mixed biomaterials from the spray head 20 and break apart droplets, thereby discouraging clogging and facilitating self clearing of spray head 20 during operation. The gas inlet 115 may be supplied with a gas propellant from a suitable gas source (not shown) to provide a desirable fluid spray pattern. The gas source may be, for example, a portable compressed gas cylinder, a pump or pressurized gas supplied from a remote source system such as an in-wall system. The gas may be carbon dioxide, nitrogen, air or other gases fit for surgical purposes. The gas may be sterile when emitted or rendered sterile prior to delivery to the device by either radiation (gamma or the like), or by filtering the gas through a suitable filter placed between the gas source and the gas inlet 115.

In operation, an operator inserts the actuating member 2 into body 5. Alternatively, actuating member 2 may be preassembled with body 5. Syringes 4, 6 are positioned against body 5 and actuating member 2 in a manner permitting the pair of positive pressure spring fingers 57, 59 to receive finger support flanges 29, 30; sidewalls 52, 54 to receive and capture syringe barrels 21, 23; and slots 69, 70 to slidably receive push flanges 27, 28. In this manner, syringes 4, 6 are held substantially parallel in body 5 without the need to rotate or twist in place syringes 4, 6 to body 5.

Once the syringes are received and captured by body 5, cannula 14 and spray head 20 are assembled to body 5 through manifold 10. Cannula 14 and sprayhead 20 may if desired be preassembled to manifold 10 during manufacturing.

The operator then connects manifold 10 to syringe outlets 31, 33 to provide an unthreaded, liquid-tight connection such that the syringe contents in syringe barrels 21, 23 are in fluid communication with cannula 14 through manifold 10.

When the delivery device 1 is fully assembled, the operator shapes the cannula 14 to a desired shape. Cannula 14 desirably is sufficiently stiff so that it will retain its shape until bent into a new shape. The shaped cannula 14 and spray head 20 are then maneuvered or navigated into a desired treatment site within the patient's body, for example, a nasal or sinus cavity or other opening, recess or passageway. Once satisfactorily positioned, an operator may, for example, depress actuating member 2 to move plunger 22, 24 toward syringe outlets 31, 33, advancing the fluid syringe contents substantially at the same time through the separate syringe barrels and out into respective fluid channels 110, 112 which maintain the fluid separation. Continued force will advance the fluids through the multi-lumen cannula 14 and into a region within spray head 20 where they mix before the mixed fluids exit spray head 20.

If compressed gas is used, it may be supplied through gas inlet 115. The gas stream passes through a lumen of multi-lumen cannula 14 into the mixing region of spray head 20. The gas stream helps atomize the mixed syringe contents resulting in much smaller droplets.

Overall, an improved multi-component delivery system is provided that allows the operator to assemble the system with ease and minimal force. The operator can position and place the syringes 4, 6 into the body 5, and connect the manifold 10 with cannula 14 and spray head 20 to the body 5 without requiring twisting or rotating to provide a liquid tight syringe connection.

The invention is further illustrated in the following non-limiting example.

EXAMPLE 1

Delivery device 1 was clamped into a suitable fixture and evaluated using a calibrated force gauge to determine assembly, disassembly and delivery forces in Lbf units. The required force was measured at least 14 times for each test described below. When combined with compressed air injected at gas inlet 115, a well-mixed spray of fine droplets in a hemispherical spray pattern was obtained.

| Test Description | Average (Lbf) | STDEV |
| --- | --- | --- |
| Actuating Member to Body Assembly Force | 2.74 | 0.48 |
| Manifold to Body Assembly Force | 9.23 | 2.27 |
| Syringe to Body Assembly Force | 14.69 | 3.07 |
| Manifold/Body Disassembly Force | 27.57 | 4.91 |
| Gel Delivery Force (Biomaterial Delivery Force) | 3.69 | 0.46 |

We claim:

1. A spray delivery system comprising:
   a) a body having a syringe-receiving portion and a finger grip portion, the body configured to receive and capture at least two liquid-containing syringes having syringe outlets and finger support flanges;
   b) an actuating member that operates on the at least two syringes to provide simultaneous syringe content delivery through the syringe outlets;
   c) a manifold with inlet openings sized and shaped to receive the syringe outlets in an unthreaded, liquid-tight connection and configured to receive liquid contents of the at least two syringes from the syringe outlets; and
   d) a spray head that receives liquids from the manifold; and wherein the at least two syringes are captured by the body and connected to the manifold without requiring threaded engagement, and the body includes positive pressure spring portions that engage the finger support flanges and maintain pressure on the finger support flanges biasing the syringe outlets into the inlet openings, thereby assisting in maintaining a liquid-tight seal at the syringe outlets.

2. The spray delivery system of claim 1, wherein the at least two syringes are held in the syringe-receiving portion by outwardly deflectable resilient sidewalls.

3. The spray delivery system of claim 1, wherein the positive pressure spring portions comprise spring fingers that maintain pressure on the at least two syringes against the finger-grip portion.

4. The spray delivery system of claim 1, wherein the body further comprises at least two syringes which contain tissue sealant components.

5. The spray delivery system of claim 4, wherein the tissue sealant components are chitosan and starch.

6. The spray delivery system of claim 1, wherein the actuating member comprises a guide rod received by the body and a thumb press oriented substantially perpendicular to the guide rod.

7. The spray delivery system of claim 6, wherein the guide rod mates with complementary grooves within the body.

8. The spray delivery system of claim 1, wherein the manifold maintains separation of the liquids until they reach the spray head.

9. The spray delivery system of claim 1, further comprising a shroud or casing that engages an outer portion of the manifold.

10. The spray delivery system of claim 9, wherein the shroud or casing surrounds and is permanently attached to the manifold.

11. The spray delivery system of claim 9, wherein the body receives and engages the manifold through a snap-fit engagement that provides leak-free attachment of the manifold without requiring an adhesive.

12. A spray delivery system comprising:
   a) a body having a syringe-receiving portion and a finger grip portion, the body configured to receive and capture at least two liquid-containing syringes having syringe outlets;
   b) an actuating member that operates on the at least two syringes to provide simultaneous syringe content delivery through the syringe outlets;
   c) a manifold with inlet openings sized and shaped to receive the syringe outlets in an unthreaded, liquid-tight connection and configured to receive liquid contents of the at least two syringes from the syringe outlets; and
   d) a spray head that receives liquids from the manifold; and
wherein the manifold comprises a channel configured to receive the body, the at least two syringes are captured by the body and connected to the manifold without requiring threaded engagement, and the body includes positive pressure spring portions that engage the syringes and maintain pressure biasing the syringe outlets into the inlet openings, thereby assisting in maintaining a liquid-tight seal at the syringe outlets.

13. A spray delivery system comprising:
   a) a body having a syringe-receiving portion and a finger grip portion, the body configured to receive and capture at least two liquid-containing syringes having syringe outlets;
   b) an actuating member that operates on the at least two syringes to provide simultaneous syringe content delivery through the syringe outlets;
   c) a manifold with inlet openings sized and shaped to receive the syringe outlets in an unthreaded, liquid-tight connection and configured to receive liquid contents of the at least two syringes from the syringe outlets; and
   d) a spray head that receives liquids from the manifold; and
wherein the syringe outlets are tapered, the manifold has first and second ports configured to receive the liquid contents, the inlet openings are in the first and second ports and are tapered to receive the syringe outlets, the at least two syringes are captured by the body and connected to the manifold without requiring threaded engagement, and the body includes positive pressure spring portions that engage the syringes and maintain pressure biasing the syringe outlets into the inlet openings, thereby assisting in maintaining a liquid-tight seal at the syringe outlets.

14. A spray delivery system comprising:
   a) a body having a syringe-receiving portion and a finger grip portion, the body configured to receive and capture at least two liquid-containing syringes having syringe outlets;
   b) an actuating member that operates on the at least two syringes to provide simultaneous syringe content delivery through the syringe outlets;
   c) a manifold with inlet openings sized and shaped to receive the syringe outlets in an unthreaded, liquid-tight connection and configured to receive liquid contents of the at least two syringes from the syringe outlets; and
   d) a spray head that receives liquids from the manifold; and
wherein the body comprises at least two deflectable projections that mate with the manifold, the at least two syringes are captured by the body and connected to the manifold without requiring threaded engagement, and the body includes positive pressure spring portions that engage the syringes and maintain pressure biasing the syringe outlets into the inlet openings, thereby assisting in maintaining a liquid-tight seal at the syringe outlets.

15. A spray delivery system comprising:
   a) a body having a syringe-receiving portion and a finger grip portion, the body configured to receive and capture at least two liquid-containing syringes having syringe outlets;
   b) an actuating member that operates on the at least two syringes to provide simultaneous syringe content delivery through the syringe outlets;
   c) a manifold with inlet openings sized and shaped to receive the syringe outlets in an unthreaded, liquid-tight connection and configured to receive liquid contents of the at least two syringes from the syringe outlets; and
   d) a spray head that receives liquids from the manifold; and
wherein the actuating member comprises a guide rod received by the body and a thumb press oriented substantially perpendicular to the guide rod, the guide rod comprises needle-like projections and latch arms to engage the body, the at least two syringes are captured by the body and connected to the manifold without requiring threaded engagement, and the body includes positive pressure spring portions that engage the syringes and maintain pressure biasing the syringe outlets into the inlet openings, thereby assisting in maintaining a liquid-tight seal at the syringe outlets.

16. The spray delivery system of claim 15, wherein the latch arms mate to a notch in the body preventing the actuating member from being removed during syringe assembly and use.

17. A spray delivery system comprising:
   a) a body having a syringe-receiving portion and a finger grip portion, the body configured to receive and capture at least two liquid-containing syringes having syringe outlets;
   b) an actuating member that operates on the at least two syringes to provide simultaneous syringe content delivery through the syringe outlets;
   c) a manifold with inlet openings sized and shaped to receive the syringe outlets in an unthreaded, liquid-tight connection and configured to receive liquid contents of the at least two syringes from the syringe outlets; and
   d) a spray head that receives liquids from the manifold; and
wherein the manifold is attached to the body with a snap fit, lock, latch, adhesive or other arrangement that makes it more difficult to disassemble the manifold from the body than to assemble the manifold onto the body, the at least two syringes are captured by the body and connected to the manifold without requiring threaded engagement, and the body includes positive pressure spring portions that engage the syringes and maintain pressure biasing the syringe outlets into the inlet openings, thereby assisting in maintaining a liquid-tight seal at the syringe outlets.

* * * * *